United States Patent [19]

Nassar

[11] Patent Number: 4,926,846
[45] Date of Patent: May 22, 1990

[54] METHOD AND DEVICE FOR LIMITING INTERMALLEOLAR EXPANSION

[76] Inventor: Lawrence G. Nassar, 33951 Glouster Cir., Farmington Hills, Mich. 48331

[21] Appl. No.: 264,529

[22] Filed: Oct. 31, 1988

[51] Int. Cl.$^5$ .................................................. A61F 3/00
[52] U.S. Cl. ................................... 128/80 H; 128/166
[58] Field of Search .................. 128/166, 80 H, 80 C

[56] References Cited

U.S. PATENT DOCUMENTS

| | | | |
|---|---|---|---|
| 2,592,739 | 4/1952 | Richardson | 128/166 |
| 2,645,222 | 7/1953 | Capossela | 128/166.5 |
| 3,383,708 | 5/1968 | Pappas | 128/166 |
| 3,508,544 | 4/1970 | Moore et al. | 2/24 |
| 3,805,781 | 4/1974 | Hoey | 128/166 |
| 4,085,746 | 4/1978 | Castiglia | 128/166 |
| 4,133,311 | 1/1979 | Karczewski | 128/80 H |
| 4,141,358 | 2/1979 | DeMarco | 128/166 |
| 4,367,733 | 1/1983 | Stromgren | 128/166 |
| 4,409,976 | 10/1983 | Pence | 128/80 H |
| 4,433,682 | 2/1984 | Badra | 128/166 |
| 4,597,395 | 7/1986 | Barlow et al. | 128/80 H |
| 4,769,854 | 9/1988 | Williams | 128/80 H |

Primary Examiner—Edgar S. Burr
Assistant Examiner—Huong Q. Pham
Attorney, Agent, or Firm—Harness, Dickey & Pierce

[57] ABSTRACT

A device for limiting the intermalleolar expansion in the mortise of a human ankle without significantly limiting the range of ankle dorsiflexion or plantar flexion.

4 Claims, 1 Drawing Sheet

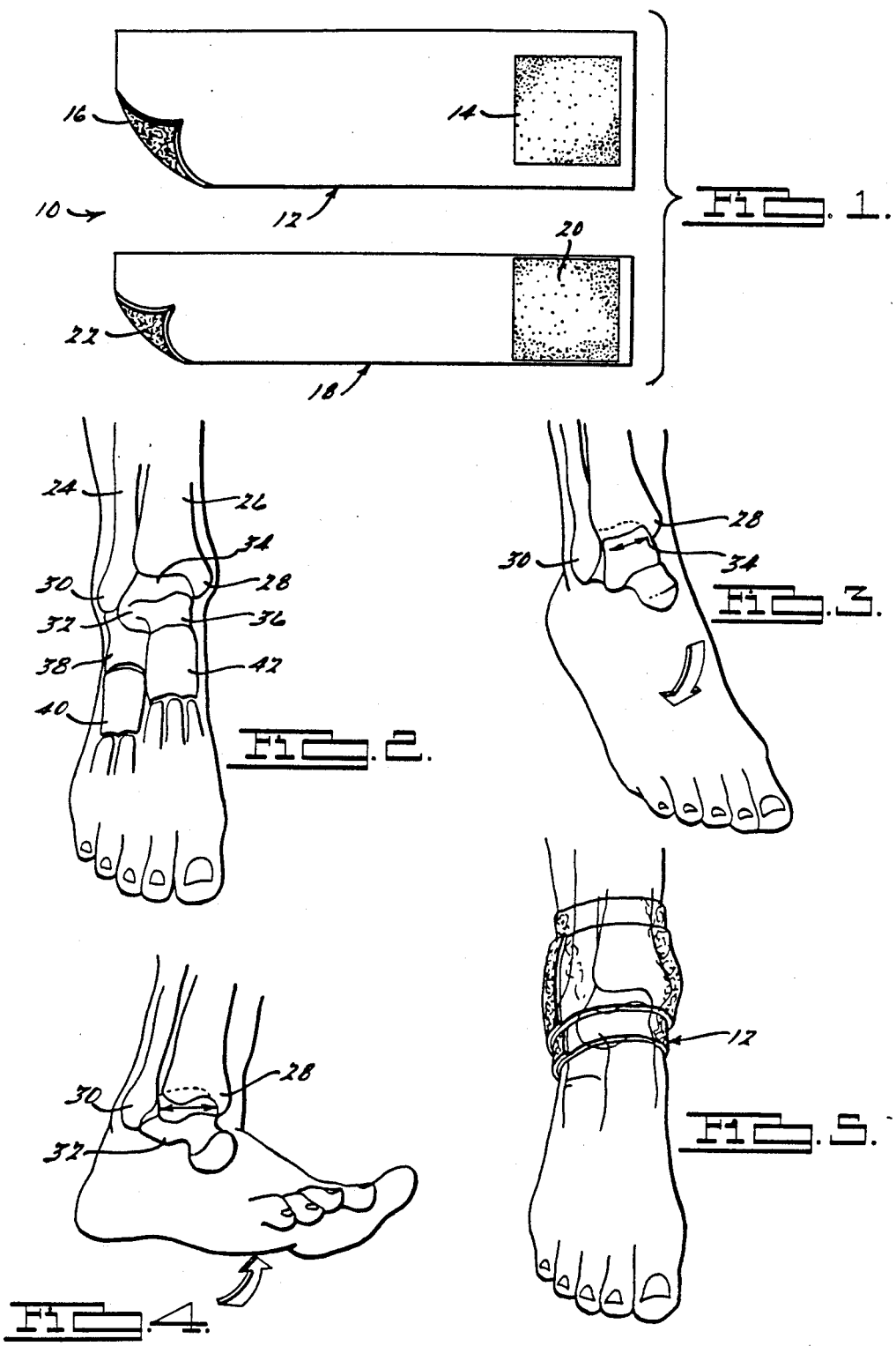

METHOD AND DEVICE FOR LIMITING INTERMALLEOLAR EXPANSION

BACKGROUND AND SUMMARY OF THE INVENTION

The present invention relates to a method and device for limiting intermalleolar expansion in the ankle joint. The ankle joint is composed of the articulations between the inferior ends of the tibia and fibula and the dome (trochlea) of the talus. The inferior ends of the tibia and fibula form the ankle mortise (socket) in which the superior articular surface of the trochlea of the talus fits. The superior articular surface of the talus is wider anteriorly than posteriorly. The articulation of the inferior ends of the tibia and fibula is called the inferior tibiofibular joint. Dorsiflexion of the ankle causes the trochlea of the talus to rock posteriorly in the mortise bringing the wide superior anterior articular surface of the trochlea into the narrower mortise forcing the lateral malleoli laterally away from the medial malleoli thus creating intermalleolar expansion. Forced hyperdorsiflexion can cause an acute sprain of the ligaments in the ankle and/or inferior tibiofibular joint. Repeated forced dorsiflexion and/or hyperdorsiflexion can cause inflammation to the ankle and/or tibiofibular joints. This is a more chronic injury and is referred to as ankle capsulitis. This problem is frequently found in persons participating athletic events such as gymnastics, volleyball, and basketball, where the participants' feet and ankles consistently absorb the shock of landing from jumps. It is the forces generated during the landing phase of a jump that typically causes the sudden forced dorsiflexion of the ankle and the resultant intermalleolar expansion.

The prior art is replete with devices, most notably a variety of wraps, which restrain ankle or foot eversion and inversion. These devices are used to stabilize the ankle to prevent eversion or inversion and act primarily to support the ligaments such as the deltoid ligament, which connect the medial malleolous and the calcaneus, or the anterior talofibular ligament, which runs from the anterior portion of the lateral malleolous to the lateral aspect of the talar neck. The prior art devices rely upon restricting unwanted ankle or foot movement, particularly the eversion or inversion of the ankle, and result in substantial limitation of all movement of the ankle, including dorsiflexion or plantar flexion. Further, prior devices are not sufficiently resistant to tensile stress to create sufficient compressive force to accomplish the same result as the present invention. In addition, prior devices have not proven to be sufficiently elastic to maintain sufficient compressive force on the tibiofibular joint capsule for sufficient durations required in sporting events. Many of the prior devices prove to be awkward and unwieldy and require significant time and effort for application and for removal.

Wherefore, it is the object of the present invention to provide a method and device for limiting intermalleolar expansion.

It is a further object of the present invention to provide a superficial wrap for the tibiofibular joint capsule which will provide and maintain sufficient tension on the joint capsule to resist expansion between the tibia and fibula due to talar intrusion caused by sudden dorsiflexion of the ankle.

It is another object of the present invention to provide an ankle wrap which is easily applied and removed, or easily adjusted for participation in athletic events.

DETAILED DESCRIPTION OF THE DRAWINGS

FIG. 1 is an elevated view of the present invention.

FIG. 2 is a dorsal view of ankle and foot demonstrating the bony anatomy of the foot and ankle.

FIG. 3 is a lateral-dorsal view of an ankle in plantar flexion demonstrating the position of the trochlea of the talus in the mortise formed by the tibia and fibula.

FIG. 4 is a lateral view of a foot and ankle in dorsiflexion demonstrating the intrusion of the talus into the mortise.

FIG. 5 is a dorsal view of an ankle and foot in plantar flexion demonstrating one embodiment of the present invention.

DETAILED DESCRIPTION OF THE PREFERRED EMBODIMENT

The invention generally relates to an improved wrap to limit intermalleolar expansion in the ankle during physical activity such as gymnastics. The invention shown generally at 10 in FIG. 1 comprises a first elongated elastomeric strap 12 having a hook and loop closure, the hooks located at 14 and the loops generally located on the opposite face of the strap 16. The invention further comprises a second elongated elastomeric strap 18 having a hook and loop closure, the hooks located at 20 and loops generally located on the opposite face of the strap 22.

FIG. 2 illustrates the bony anatomy of the foot and ankle. As can be seen the fibula 24 extends farther than the tibia 26. The distal end of the tibia 26 is known as the medial malleolous 28, and the distal end of the fibula is known as the lateral malleolous 30. The medial malleolous 28 and the lateral malleolous 30 form the mortise in which is seated the talus 32. The dorsum of the talus is known as the trochlea of the talus 34, and the middle portion of the talus is known as the neck of the talus 36. Beneath the talus lies the calcaneus 38, and the calcaneus distally articulates with the cuboid bone 40. Anterior of the talus 36 is the navicular bone 42 which articulates laterally with the cuboid bone 40 and distally with the three cuneiforms which articulate distally with the first three metatarsal bones. The cuboid bone 40 articulates distally with the fourth and fifth metatarsal bones.

FIG. 3 illustrates a foot and ankle in the plantar flexed position illustrating the position of the trochlea of the talus 34 within the mortise and the intermalleolar distance between the medial malleolous 28 and the lateral malleolous 30.

FIG. 4 illustrates a foot and ankle in the dorsiflexed position, such as would occur upon a gymnast's landing, demonstrating the intrusion of the talus 32 into the mortise. The intrusion of the trochlea 34 causes the lateral malleolous 30 and the medial malleolous 28 to separate, causing intermalleolar expansion.

A method for testing for an injury caused by intermalleolar expansion due to talus intrusion into the mortise is conducted by having the examinee remove all weight from the foot and ankle being tested and by pressing or tapping the ball of the foot upward to dorsiflex the foot and ankle to determine whether there is pain from such motion. If there is such pain, the test is repeated while manually applying compressive pressure upon each side of the ankle, manually restricting the intermalleolar expansion. If the ankle joint or tibiofibular joint is injured due to intermalleolar expansion, the amount of pain should be dramatically reduced during the second test.

FIG. 5 illustrates an embodiment of the present invention applied to an ankle in order to provide the necessary compressive force to the mortise to restrict intermalleolar expansion. The first strap 12 is applied by manually securing one end against the ankle at the lateral malleolous and applying tension to the length of the strap while wrapping the ankle with the strap, and by securing the strap in place by pressing the hook and loop closure together. The second strap 18 is similarly applied over top of the first strap, beginning either by manually securing one end of the second strap to the opposite side of the ankle or by manually securing the end at the same side of the ankle (as shown in FIG. 5).

In order to facilitate location of the second strap, and to assist in securing the first end of the second strap into position while applying tension during wrapping of the second strap, a third hook and loop closure may be provided, one portion of which is located on the first strap on the exterior face near the midway point of the strap such that it would automatically be located approximately opposite the beginning of the first strap. The second strap would then be provided with the opposing portion of the hook and loop fastener at the interior face of its first end such that it may be pressed upon the other portion of the third hook and loop closure and thusly automatically positioned and secured into place for wrapping.

The second strap adds a great deal of compressive force on the mortise such that it is a dramatic improvement over the use of a single strap. The second strap is narrower than the first such that the tensile force is more concentrated upon the mortise.

Significant testing upon gymnasts has proved that the two strap system is vastly superior to prior art wrappings. "Ace" bandage-type wrappings proved insufficient to provide the necessary tension to restrict intermalleolar expansion and were too bulky for gymnastic-type applications. Athletic tape can provide the necessary compressive force, but tape lasts a very short period of time before it will loosen and lose effectiveness. The present invention can be use in conjunction with athletic tape around the ankle.

In the preferred embodiment of the present invention, the first strap 12 is 12" long and 3" wide and is made of ⅛" thick neoprene. The second is preferred to be 2" wide and 12" long and also of ⅛" thick neoprene. The length of the straps are extra long so that they can be cut to fit each ankle in a customized fashion.

It has been found in testing that a single strap of a double length wrap twice around the ankle will not provide the same compressive force to restrict intermalleolar expansion, even providing a intermediate closure after the first revolution.

Although it is apparent that the preferred embodiment of the present invention is well calculated to provide the features and advantages stated above, it will be appreciated that the invention is susceptible to modification, variation, and change without departing from the proper scope or fair meaning of the appended claims.

What is claimed is:

1. Method of providing a compressive force on a tibiofibular joint capsule of an ankle to limit intermalleolar expansion comprising:

providing a first independent length of elastomeric material having a length slightly larger than the circumference of the exterior of the tibiofibular joint;

applying said first length of elastomeric material by placing one end against and centering the width of said first length relative to the lateral malleolus protrusion, wrapping said first length circumferentially around the ankle one time while applying tension along the length of said first length, and closing said first length at its opposing ends;

providing a second independent length of elastomeric material having a length slightly less than the length of said first length and a width less than but at least half of the width of said first length;

applying said second length of elastomeric material by placing one end against and centering the width of said second length relative to and upon the exterior surface of the first length and to the medial malleolus protrusion, wrapping said second length circumferentially around the ankle one time, while applying tension along the length of said second length and closing said second length at its opposing ends.

2. An exterior wrap for limiting intermalleolar expansion of a tibiofibular joint capsule without limiting said joint capsule's range of motion comprising:

a first independent elastomeric strip having two ends and a length approximately equal to the circumference of the external surface of said joint capsule plus an additional length to accommodate a first closure means, locating means disposed on said first steps;

said first closure means for said first independent elastomeric strip located at the ends of said first elastomeric strip;

a second independent elastomeric strip applied upon the exterior surface of said first independent elastomeric strip said second strip having two ends, the length of said second strip being slightly less than the length of said first strip and the width of said second strip being less than but at least half of the width of said first strip;

an orientation means disposed on said second independent elastomeric strip engageable with said locating means; and a second closure means for said second independent elastomeric strip located at the ends of said second elastomeric strip.

3. The invention of claim 2 wherein said first independent elastomeric strip is approximately 1.5 times the width of said second independent elastomeric strip.

4. The invention of claim 2 wherein said first strip is approximately three inches wide and said second strip is approximately two inches wide.

* * * * *

UNITED STATES PATENT AND TRADEMARK OFFICE
CERTIFICATE OF CORRECTION

PATENT NO. : 4,926,846

DATED : May 22, 1990

INVENTOR(S) : Lawrence G. Nassar

It is certified that error appears in the above-identified patent and that said Letters Patent is hereby corrected as shown below:

Column 4, line 39, Claim 2, "steps" should be --strip--.

Column 4, line 45, Claim 2, after "strip" (first occurrence) insert --,--.

Column 4, line 61, Claim 4, delete "approximately".

Signed and Sealed this

Seventeenth Day of March, 1992

Attest:

HARRY F. MANBECK, JR.

*Attesting Officer*      *Commissioner of Patents and Trademarks*